United States Patent [19]

Marbet

[11] 4,026,910
[45] May 31, 1977

[54] OXIDATION PROCESS USING NICKEL PEROXIDE OXIDIZING AGENTS

[75] Inventor: Roman Marbet, Riehen, Switzerland

[73] Assignee: Hoffmann-La Roche Inc., Nutley, N.J.

[22] Filed: July 23, 1975

[21] Appl. No.: 598,307

[30] Foreign Application Priority Data

Aug. 5, 1974 Switzerland .................. 10690/74

[52] U.S. Cl. .................. 260/410.9 R; 260/603 R; 260/586 P; 260/592; 260/590 C; 260/590 D; 260/476 R; 260/491; 260/591
[51] Int. Cl.$^2$ .................. C11C 3/02; C07C 45/16
[58] Field of Search ..... 260/406, 410.9 R, 603 HC, 260/586 P, 592, 590, 476 R, 491, 405.5; 423/582

[56] References Cited

UNITED STATES PATENTS

| | | | |
|---|---|---|---|
| 2,303,550 | 12/1942 | Houghton | 260/586 P |
| 2,371,794 | 3/1945 | Boyd | 260/586 P |
| 3,047,630 | 7/1962 | Addy | 260/586 P |
| 3,226,390 | 12/1965 | Nahagawa | 260/603 HF |

Primary Examiner—Winston A. Douglas
Assistant Examiner—John F. Niebling
Attorney, Agent, or Firm—Samuel L. Welt; Bernard S. Leon; Richard A. Gaither

[57] ABSTRACT

Preparation of a nickel peroxide oxidizing agent from nickel hydroxide and its use in oxidizing $\alpha,\beta$-unsaturated alcohols to the corresponding carbonyl compounds.

6 Claims, No Drawings

OXIDATION PROCESS USING NICKEL PEROXIDE OXIDIZING AGENTS

BACKGROUND OF THE INVENTION

In the past nickel peroxide oxidizing agents have been generally prepared as described in U.S. Pat. No. 3,226,390 Nakagawa et al. In this patent the metal peroxide is formed by treating a nickel salt with an alkali metal hypohalite or persulphate and is used for oxidizing an unsaturated alcohol to the corresponding carbonyl compounds. For example it has been reported by Nakagawa et al. that Vitamin A alcohol was oxidized with this nickel peroxide to Vitamin A aldehyde.

By utilizing the nickel peroxide, oxidizing agent mentioned inaccordance with Nakagawa et al., the oxidation of $\alpha,\beta$-unsaturated alcohols to the corresponding carbonyl compounds can be carried out at relatively high temperatures i.e. at 0° C and above i.e. from 0° to 90° C and especially between 30° to 70° C. For example geraniol can be converted into citral at temperatures at 50° C within 6 hours.

However, there is a great disadvantage of utilizing such high temperatures and reaction times especially since many of the $\alpha,\beta$-unsaturated alcohols are temperature sensitive. This sensitivity promotes decomposition especially when high temperatures and reaction times are utilized. It has long been desired to provide an oxidizing agent which can oxidize $\alpha,\beta$-unsaturated alcohols at very low temperatures i.e. below 0° C.

SUMMARY OF INVENTION

Inaccordance with this invention, it has been discovered that where a nickel peroxide oxidizing agent is prepared by first oxidizing nickel(II)hydroxide containing starting material with a strong oxidizing agent in an aqueous medium to form nickel peroxide as a precipitate and then drying the nickel peroxide precipitate to a weight of a least 110 grams per mole of the nickel(II) hydroxide in the starting material, while carrying out said drying and oxidizing steps with the exclusion of carbon dioxide and water soluble carbonates, this nickel peroxide oxidizing agent can be utilized to oxidize $\alpha,\beta$-unsaturated alcohols to the corresponding $\alpha,\beta$-unsaturated carbonyl compounds also at low temperatures utilizing relatively low reaction times i.e. within 5 minutes and generally from 15 minutes to 3 hours. Furthermore the yields of the $\alpha,\beta$-unsaturated carbonyl compounds under these conditions are mostly quantitative. For example, this nickel peroxide preparation quantitatively oxidizes geraniol to citral at −25° C within 90 minutes. The yield is practically quantitative even when the reaction is carried out at −50° C for 5 hours.

Inaccordance into this invention, the nickel peroxide oxidizing agent can be utilized to oxidize any $\alpha,\beta$-unsaturated alcohol to the corresponding $\alpha,\beta$-unsaturated oxo compound.

In accordance into a preferred embodiment of this invention an $\alpha,\beta$-unsaturated alcohol of the formula:

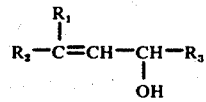

wherein
R₁ is individually hydrogen or lower alkyl; R₂ is individually hydrocarbyl, cyclohydrocarbyl or cyclohydrocarbyl substituted hydrocarbyl; R₁ taken together with R₂ and their attached carbon atom form a cyclohydrocarbyl; R₃ is hydrogen, hydrocarbyl, cyclohydrocarbyl or cyclohydrocarbyl substituted hydrocarbyl; said hydrocarbyl and cyclohydrocarbyl being unsubstituted or substituted in one or more positions with lower alkyl, lower alkoxy, hydroxy, oxo, acetalized oxo, lower alkanoyl, aroyl, lower alkanoyloxy, or aroyloxy;

is oxidized to $\alpha,\beta$-unsaturated carbonyl compound of the formula:

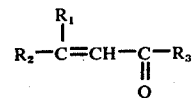

wherein
R₁, R₂ and R₃ are as above.

DETAILED DESCRIPTION OF THE INVENTION

As used throughout this application, the term "hydrocarbyl" denotes a monovalent, straight chain or branched chain aliphatic substituent consisting solely of carbon and hydrogen. The hydrocarbyl group can be saturated or unsaturated in one or more positions. Among the hydrocarbyl groups are included alkyl groups containing from 1 to 30 carbon atoms and alkenyl and alkynyl groups containing from 2 to 30 carbon atoms. The alkyl alkenyl or alkynyl groups can be unsubstituted or substituted, preferably from 1 to 7, on one or more, positions with lower alkyl or from 1 to 3 positions with lower alkoxy, hydroxy, oxo, acetalized oxo, lower alkanoyl, aroyl, lower alkanoyloxy, or aroyloxy groups. Among the preferred hydrocarbyl groups are included lower alkyls and groups having an isoprene or isoprenelike structure. Among the preferred substituted or unsubstituted hydrocarbyl groups denoted by R₂ and R₃ are included:
  methyl;
  4-methyl-pent-3-enyl;
  3,4-dimethyl-pent-3-enyl;
  1-ethyl-4-methyl-pent-3-enyl;
  4-methoxy-4-methyl-pentyl;
  4,8-dimethyl-nona-3,7-dienyl;
  4,8,12-trimethyl-tridecyl;
  4,8,12-trimethyl-trideca-3,7,11-trienyl; and
  5-acetoxy-3-methyl-3-penten-1-ynyl.

As also used throughout this application, the term "cyclohydrocarbyl" denotes a monovalent, mono- or poly-cycloaliphatic or aryl substituent consisting solely of carbon and hydrogen. The cycloaliphatic group can be saturated or unsaturated in one or more positions. The cyclohydrocarbyl substituent defined by R₁, R₂ and R₃ can be unsubstituted or substituted in one or more, preferably from 1 to 3 positions, with lower alkyl, lower alkoxy, hydroxy, oxo, acetalized oxo, lower alkanoyl, aroyl, lower alkanoyloxy or aroyloxy groups. The substituted and unsubstituted cyclohydrocarbyl can include from 3 to 30 carbon atoms. Among the preferred monocycloaliphatic substituents which are defined by R₁, R₂ and R₃ are included the cycloalkyl or cycloalkenyl groups containing from 3 to 10, preferably 3 to 7, carbon atoms, i.e., cyclohexyl, cyclopropyl, cycloheptyl, 3-methyl-cyclohex-3-en-1-yl; and 4-methyl-cyclohex-3-en-1-yl and cyclohexenyl. Among the preferred aryl substituents which are defined by R₁, R₂ and $R_3$ being cyclohydrocarbyl is phenyl and naphthyl. In the compounds of formula II where $R_1$ and $R_2$ are joined together to form an unsubstituted or substituted monocycloaliphatic substituent, the preferred compounds are:

4-ethynyl-4-hydroxy-l-oxo-3,5,5-trimethyl-cyclohex-2-ene; and 4-ethynyl-4-hydroxy-1,1-ethylenedioxy-3,5,5-trimethyl-cyclohex-2-ene.

The term cyclohydrocarbyl also includes polycycloaliphatic substituents, i.e., a cycloalkyl group condensed with one or more saturated or unsaturated cycloalkyl groups. Where $R_1$ and $R_2$ taken together with their attached carbon atom form a cyclohydrocarbyl substituent, the substituent can be a monocycloaliphatic group or a monocycloaliphatic group condensed with one or more cyclohydrocarbyl groups. These groups include:

17alpha-ethynyl-3beta,17beta-dihydroxy-androst-5-ene;

17alpha-ethynyl-17beta-hydroxy-13beta-methyl-gon-5(lo)-en-3-one; and norgestrel.

As further used throughout this application, the term "cyclohydrocarbyl substituted hydrocarbyl" denotes cyclohydrocarbyl substituted hydrocarbyl groups wherein cyclohydrocarbyl and hydrocarbyl are defined as above. Both the cyclohydrocarbyl and hydrocarbyl groups can be unsubstituted or either one or both of the hydrocarbyl and cyclohydrocarbyl groups can be substituted in one or more positions, preferably is 1 to 7 positions, with lower alkyl, and in from 1 to 3 positions with lower alkoxy, hydroxy, oxo, ketalized oxo, lower alkanoyl, aroyl, lower alkanoyloxy or aroyloxy.

Among the preferred cyclohydrocarbyl substituted hydrocarbyl substituents defined by $R_2$ and $R_3$ are the groups wherein the hydrocarbyl moiety has an isoprene or isoprene-like structure, such as:

2-(2,6,6-trimethyl-cyclohex-l-en-l-yl)-vinyl;

2-(4-oxo-2,6,6-trimethyl-cyclohex-l-en-l-yl)-vinyl;

2-(4,4-ethylenedioxy-2,6,6-trimethyl-cyclohex-l-en-l-yl)-vinyl;

6-(2,6,6-trimethyl-cyclohex-l-en-l-yl)-4-methyl-hexan-1,3,5-trienyl;

6-(4-oxo-2,6,6-trimethyl-cyclohex-l-en-l-yl)-4-methyl-hexa-1,3,5-trienyl; and 6-(4,4-ethylenedioxy-2,6,6-trimethyl-cyclohex-l-en-l-yl)-4-methyl-hexa-1,3,5-trienyl groups.

Among the substituted and unsubstituted hydrocarbyl groups defined by $R_3$ are:

methyl;

propyl;

ethynyl;

2-hydroxy-prop-2-yl; and 2,6-dimethyl-hepta-1,3,5-trienyl.

As further used throughout this application, the term "lower alkyl" comprehends branched chain and straight chain, saturated aliphatic hydrocarbyl groups containing 1 to 7 carbon atoms, such as methyl, ethyl, propyl and isopropyl. As also used herein, the term "lower alkoxy" comprehends lower alkyloxy groups containing 1 to 7 carbon atoms such as methoxy and isopropoxy. As further used herein, the term "lower alkanoyl" comprehends lower alkyl acyl groups containing 2 to 7 carbon atoms such as acetyl, propionyl, and butyryl. As still further used herein, the term "aroyl" comprehends monocyclic, aromatic hydrocarbon acyl groups which may be unsubstituted or substituted in one or more positions with an alkylamino, lower alkyl, halogen, trifluoromethyl, nitro or lower alkoxy. The preferred aroyl is benzoyl. Also herein, the term "lower alkanoyloxy" comprehends lower alkyl acyloxy groups containing 2 to 7 carbon atoms such as acetoxy and propionyloxy. Further herein, the "aroyloxy" comprehends groups such as benzoyloxy. Still further herein, the term "cycloalkyl" comprehends cycloaliphatic groups of 3 to 7 carbon atoms, such as cyclohexyl. Also herein, the term "aryl" signifies mono nuclear aromatic hydrocarbon groups such as phenyl, tolyl, etc., which can be unsubstituted in one or more positions with lower alkyl, halogen, trifluoromethyl, nitro or lower alkoxy, alkylamino, or polynuclear aryl groups such as naphthyl, anthryl, phenanthryl, azulyl, etc., which can be unsubstituted or substituted with one or more of the aforementioned groups. The preferred aryl substituents are phenyl or naphthyl which can be unsubstituted or substituted in one or more positions with lower alkyl, nitro, alkylamino, halo, trifluoromethyl, or lower alkoxy. The term "alkali metal" includy all alkali metals such as lithium, sodium, potassium, etc.

The term "halogen" denotes all four halogens, i.e., chlorine, fluorine, bromine or iodine, with chlorine and bromine being preferred.

As still further used throughout this application, the term "aliphatic", with reference to a hydrocarbyl or cyclohydrocarbyl group, denotes substituents containing no aromatic unsaturation but which can be otherwise saturated or unsaturated, i.e., an alkyl or a group containing olefinic and/or acetylenic unsaturation. Also herein, the term "acetalized oxo" comprehends derivatives of an oxo group formed by reaction thereof with a lower alkanediol, preferably ethylene glycol, or a lower alkanol, preferably methanol, to yield a lower alkylenedioxy group. The preferred lower alkylenedioxy groups are the groups having 2 to 4 carbon atoms, particularly ethylenedioxy.

Among the preferred alcohols of formula I which can be oxidized in accordance with this invention include both primary and secondary alcohols, especially allyl alcohols and benzyl alcohols. In particular, the process can be utilized with alcohols such as benzyl alcohol, geraniol, phytol, 8-hydroxy-2,6-dimethyl-octa-2,4,6-trien-l-oic acid ethyl ester, 8-hydroxy-2,6-dimethyl-octa-2,4,6-trien-l-al acetal, vitamin A alcohol, ionol and the like. The manufacture of all-trans vitamin A aldehyde by oxidation of all-trans vitamin A alcohol at temperatures below 0° C, especially at −20° to −30° C, is an especially preferred application of the nickel peroxide obtained in accordance with the invention.

The present invention is concerned with a process for the manufacture of or for the regeneration of nickel peroxide by treating nickel (II) hydroxide with strong oxidising agents and drying the moist product obtained, said process comprising carrying out the oxidation and the drying with the exclusion of carbon dioxide and of water soluble carbonates and the drying being carried out up to a weight of not less than 110 g per mole of nickel (II) hydroxide originally used.

In a second aspect, the present invention is concerned with a process for the manufacture of $\alpha,\beta$-unsaturated carbonyl compounds (aldehydes and ketones) by the oxidation of $\alpha,\beta$-unsaturated alsohols, said process being carried out using a nickel peroxide produced in the manner described earlier as the oxidising agent.

Nickel peroxide is a substance which is known per se and which has also already been used for the oxidation of α,β-unsaturated alcohols. The exact structure of nickel peroxide is, however, unknown.

In general, there is understood by nickel peroxide those black-coloured nickel oxides or hydroxides which are obtained by the reaction between a strong oxidising agent such as an alkali hypohalite, alkali persulphate or ozone and nickel oxide or freshly precipitated nickel hydroxide in an aqueous alkaline medium and the subsequent drying the water-moist product to a constant weight. The formula Ni(OH)$_3$ (M.Wt. = 110) or Ni$_2$O$_3$. 3H$_2$O (M.Wt. = 219) is assigned to nickel peroxide. The formula

(M.Wt. = 91.7) or Ni$_3$O$_2$(OH)$_4$ (M.Wt. = 276( is also assumed to be probable. From one mole of nickel salt there are accordingly obtained 92–110 g of dry nickel peroxide, depending on which formula is taken to be correct.

As obtained according to the aforementioned method, nickel peroxide does not, however, usually contain ca $1.10^{-2}$ gram-atoms of active oxygen per gram of preparation as would be expected, but only $0.3-0.4.10^{-2}$ gram-atoms, detected by the customary sodium thiosulphate titration of the iodine which is liberated by the reaction between nickel peroxide and potassium iodide in glacial acetic acid solution.

It can therefore be assumed that in the nickel peroxide obtained according to the usual method there is still present ca 50% of nickel (II) hydroxide

(M.Wt. = 92.7). From 1 mole of nickel salt solution there could thus be expected, after conversion into nickel peroxide and complete drying of the preparation, only a yield of 92–101 g of the oxidising agent, depending on which of the aforementioned formulae is assumed for the pure nickel peroxide.

The nickel hydroxide utilized as starting material in this invention can be prepared from a nickel salt such as nickel sulphate, nickel carbonate, etc. The preparation of the nickel (II) hydroxide is carried out by treating the water soluble salt in a conventional manner in an aqueous solution with a base such as an alkali metal hydroxide. On the other hand the nickel (II) hydroxide containing starting material can be prepared from reduced nickel peroxide when it is used as a oxidizing agent as in the oxidation of an α,β-unsaturated alcohol to an α,β-unsaturated aldehyde. The spent oxidizing agent nickel peroxide, now contains nickel (II) hydroxide which can be regenerated for use, inaccordance with this invention, in the same manner as the nickel (II) hydroxide starting material prepared from the water soluble nickel salt.

This nickel peroxide is produced, as mentioned hereinbefore, by carrying out the oxidation of nickel (II) hydroxide or of the previously used nickel peroxide, as well as the subsequent drying of the moist product, with the exclusion of carbon dioxide and water soluble carbonates and further drying the product obtained only up to a weight of not less than 110 g per mole of nickel (II) hydroxide present in the starting material.

It has been found that nickel peroxides having a dry weight lower than 110 g per mole of nickel (II) hydroxide can, in fact, always have the expected iodometrically detectable content of active oxygen and is capable of oxidising unsaturated alcohols at temperatures between 0°–90° C, but that, in contrast thereto, nickel peroxide preparations having a dry weight of more than 110 g per mole of nickel (II) hydroxide used can surprisingly also convert the corresponding alcohols into aldehydes or ketones even at temperatures below 0° C. Nickel peroxide preparations having a dry weight of 120–140 g have proved to be especially active. In the case of nickel peroxide preparations having a weight higher than 140 g, the activity slowly decreases. Such preparations (with, for example, a dry weight of 150–160 g) are still in fact active at below 0° C, but proportionally more nickel peroxide has to be used than with optimally dried nickel peroxide.

After the use of the nickel peroxide manufactured in accordance with the invention in the manufacture of α,β-unsaturated carbonyl compounds, the spent nickel peroxide preparation can be regenerated by treatment in a manner known per se with a strong oxidising agent, this oxidation and the subsequent drying of the moist product again being carried out in the absence of carbon dioxide and of water-soluble carbonates and the drying again being carried out only up to a weight of over 110 g per mole of nickel (II) hydroxide present in the starting material.

The temperature for the manufaction or regeneration of nickel peroxide may vary from 0° to 50° C. However because of the decompossibility of the nickel peroxide, temperatures of from 0° C to 30° C are generally preferred.

In the drying step, it is necessary that it is carried out with the exclusion of $CO_2$ and water soluble carbonates. This is affected by drying under an inert gas atmosphere such as nitrogen or a noble gas. Any conventional noble gas can be utilized to provide the inert atmosphere which excludes $CO_2$ and water soluble carbonates from the reaction medium. Among the preferred noble gases are helium, argon, neon, etc. The drying is most expediently carried out by blowing the gas stream through the product. Temperatures of from 0° to 40° C as utilized during the drying step, with temperatures of from 0° to 30° C being generally preferred.

In order to facilitate the filtration of the nickel peroxide and to increase its surface area, the manufacture of the preparation may also be carried out in the presence of an inert carrier such as, for example, graphite.

The amount of the strong oxidising agent used in the manufacture of or for the regeneration of the expended nickel peroxide is also responsible for the iodometrically detected content of active oxygen. This does, however, not usually exceed ca. 8%.

Sodium or potassium hypochlorite is the preferred strong oxidising agent. In an especially preferred embodiment, the alkali hypochlorite is prepared in situ. According to this embodiment, nickel (II) hydroxide or the spent nickel peroxide to be regenerated is stirred with aqueous sodium hydroxide solution and treated with chlorine gas at 0°–5° C until the pH drops to 9–11. Then, the resulting nickel peroxide is separated by filtration or centrifugation. After washing with water, the nickel peroxide is dried in a gas stream up to the weight specified hereinbefore.

The nickel peroxide manufactured in accordance with the present invention can be used for the oxidation of $\alpha,\beta$-unsaturated alcohols to the corresponding carbonyl compounds. In particular, this nickel peroxide can also be used at a temperature below 0° C, especially at $-20°$ to $-40°$ C.

The oxidation can be carried out by stirring the nickel peroxide with the $\alpha,\beta$-unsaturated alcohol dissolved in an inert organic solvent. Such solvents include, for example, aliphatic hydrocarbons (e.g. pentane, hexane, heptane and the like) and aromatic hydrocarbons (e.g. toluene and the like). Halogenated hydrocarbons (e.g. methylene chloride or chlorobenzene) can also be used. Where $R_3$ is hydrogen, the oxidation step is carried out at temperatures below 0° C i.e. from 0° to $-100°$ C. While higher temperatures can be utilized i.e. 90° C utilizing the oxidizing agent of this invention makes the use of these high temperatures unecessary. This is extremely advantageous since temperatures of above 0° C causes decomposition and loss of yield.

Where $R_3$ is other than hydrogen, the step can be carried out at relatively low temperatures, i.e. 0° to 50° C. Temperatures of greater than 50° C can be utilized in the case where $R_3$ is other than hydrogen, i.e. temperatures of up to 90° C can be utilized, however at these high temperatures, many compounds decompose.

The amount of the nickel peroxide manufactured in accordance with the present invention required for the oxidation is governed by the content of active oxygen therein. In general, it is calculated at about 1.5–2.5, especially at about 1.8–2.2, equivalents of oxygen per mole of $\alpha,\beta$-unsaturated alcohol.

The following Examples illustrate the present invention. In each of Examples 1–11, the characterisation of the product is carried out according to the following 3 criteria:
1. Weight;
2. % of active oxygen (iodometrically determined);
3. Sample oxidation with 1/100 mole of geraniol by the procedure described in Example 12.

EXAMPLE 1

56.2 g (0.2 mole) of nickel sulphate ($NiSO_4.7H_2O$) are dissolved in 200 ml of water. The solution is cooled to 0°–5° C and treated within about 15 minutes while stirring with a solution of 16 g of sodium hydroxide in 40 ml of water. The mixture has a pH 9 and contains 0.2 moles of nickel hydroxide. There are now added at 0°–5° C within ca 15 minutes 125 ml of a 5.5% by weight aqueous sodium hypochlorite solution and the mixture is stirred for a further 15 minutes at 0°–5° C. The black product is filtered off in a pressure filter under 1.4 atmospheres of nitrogen, washed twice with 500 ml of water each time and then dried to a dry weight of 24 g within 3 hours by blowing nitrogen through the product. Iodometric titration: 6.1% of active oxygen. Sample oxidation with 4.4 g of nickel peroxide: geraniol is quantitatively converted into citral.

EXAMPLE 2

281 g (1 mole) of nickel sulphate ($NiSO_4.7H_2O$) in 1250 ml of water are treated at 0°–5° C with a solution of 120 g (3 mole) of sodium hydroxide in 250 ml of water to produce nickel hydroxide (1 mole). While controlling the pH with a glass electrode, chlorine gas is now fed in until a pH decrease from ca 13.5 to ca 11 indicates the consumption of the excess sodium hydroxide. The mixture is now stirred for 30 minutes at 0°–5° C, no further chlorine gas being led in and the pH of the mixture being controlled such that it does not fall below ca 9. The mixture is then filtered through a pressure filter in the manner described in Example 1, washed three times with 1 liter of water and then dried in a nitrogen stream.
Dry weight: 121 g.
Iodometric titration: 5.8% of active oxygen.
Sample oxidation with 5.5 g of nickel peroxide: quantitative conversion.

EXAMPLE 3

By the procedure of Example 2, 281 g of nickel sulphate ($NiSO_4.7H_2O$) are reacted with 140 g (3.5 mole) of sodium hydroxide, then treated with chlorine gas and worked-up in the manner described earlier in this Example.
Dry weight: 115 g
Iodometric titration: 7.3% of active oxygen.
Sample oxidation with 4.4 g of nickel peroxide: quantitative conversion.

EXAMPLE 4

By the procedure of Example 2, 281 g of nickel sulphate ($NiSO_4.7H_2O$) are reacted with 160 g (4 mole) of sodium hydroxide and then treated with chlorine gas. Working-up and drying is carried out in the manner described earlier in this Example 2.
Dry weight: 120 g.
Iodometric titration: 7.3% of active oxygen.
Sample oxidation with 4.3 g of nickel peroxide: quantitative conversion.

EXAMPLE 5

By the procedure of Example 2, 281 g of nickel sulphate ($NiSO_4.7H_2O$) are reacted with 200 g (5 mole) of sodium hydroxide and then treated with chlorine gas. Working-up and drying is carried out in the manner described in Example 2 to produce nickel peroxide.
Dry weight: 120 g.
Iodometric titration: 7.5% of active oxygen.
Sample oxidation with 4.2 g of nickel peroxide: quantitative conversion.

EXAMPLE 6

By the procedure of Example 2, 281 g of nickel sulphate ($NiSO_4.7H_2O$) are reacted with 240 g (6 mole) of sodium hydroxide. Working-up and drying is carried out in the manner described in Example 2 to produce nickel peroxide.
Dry weight: 154 g.
Iodometric titration: 6.35% of active oxygen.
Sample oxidation with 6.5 g of nickel peroxide: quantitative conversion.

EXAMPLE 7

56.2 g (0.2 mole) of nickel sulphate ($NiSO_4.7H_2O$) in 200 ml of water are treated at 0°–5° C within 15 minutes with a solution of 28 g of sodium hydroxide in 50 ml of water. While controlling the pH with a glass electrode, ca 6 ml of bromine are allowed to drop in at 0°–5° C within ca 40 minutes until the pH falls to 11–12. The mixture is stirred for a further 30 minutes while cooling and then filtered through a pressure filter. The residue is washed twice with 500 ml of water each time and dried in a gas stream under nitrogen to produce nickel peroxide.
Dry weight: 24 g.
Iodometric titration: 6.8% of active oxygen.
Sample oxidation with 4.7 g of nickel peroxide: quantitative conversion.

EXAMPLE 8

52.5 g (0.2 mole) of nickel sulphate ($NiSO_4.6H_2O$) in 200 ml of water are treated at 0°–5° C with 32 g of sodium hydroxide in 100 ml of water. There is then added at 0°–5° C within 45 minutes a solution of 92.2 g (0.4 mole) of sodium persulphate ($Na_2S_2O_8$) in 200 ml of water and the mixture is stirred for a further 45 minutes. The mixtures is filtered through a presssure filter under 1.4 atmospheres of nitrogen, washed three times with 500 ml of water each time and dried for 3–4 hours in a nitrogen stream to produce the nickel peroxide.
Dry weight: 24 g.
Iodemetric titration: 6.9% of active oxygen.
Sample oxidation with 4.6 g of nickel peroxide: quantitative conversion.

EXAMPLE 9

56.2 (0.2 mole) of nickel sulphate ($NiSO_4.7H_2O$) in 200 ml of water are treated with 24 g of graphite. The mixture is stirred at 0°–5° C with a solution of 28 g of sodium hydroxide in 50 ml of water. Chlorine gas is fed in at 0°–5° C until the pH of 13.5 has fallen to 9–11. After stirring at 0°–5° C for a further 30 minutes, the mixture is filtered through a pressure filter under 1.4 atmospheres of nitrogen, washed twice with 500 ml of water each time and finally dried in a nitrogen stream within 3–4 hours to produce nickel perxide.
Dry weight: 49 g.
Iodometric titration: 3.2% of active oxygen.
Sample oxidation with 10 g of nickel peroxide: quantitative conversion.

EXAMPLE 10

251 g of basic nickel carbonate [$NiCO_3.2Ni(OH)_2.4H_2O$; M.Wt. = 376] are suspended in 2 liters of water and brought into solution at room temperature within ca 30 minutes with 340 ml (ca 4.8 mole) of 64% by weight aqueous nitric acid. The thus-obtained solution of 2 mole of nickel nitrate is treated at 0°–5° C within ca 30 minutes with a solution of 312 g (7.8 mole) of sodium hydroxide in 700 ml of water. Chlorine gas is then fed in at 0°–5° C within about 40 minutes until the pH of 13–14 has fallen to ca 11. After about 5 minutes, the pH remains constant at about 10.5 and the mixture is filtered through a pressure filter under 1.4 atmospheres of nitrogen. The residue is washed twice with 1 liter of water each time and once with 2 liters of water, then dried under nitrogen in a flowing gas stream for 12 –14 hours until a weight of 300 g of the nickel peroxide is reached (corresponding to 150 g per mole of nickel nitrate originally present).
Iodometric titration: 5.9% of active oxygen.
Sample oxidation with 5.4 g of nickel peroxide: quantitative conversion.

EXAMPLE 11

56.2 g (0.2 mole) of nickel sulphate ($NiSO_4.7H_2O$) in 200 ml of water are treated at room temperature within 15 minutes with a solution of 32 g of sodium hydroxide in 100 ml of water. 90 mmole of ozone per hour are led into the thus-obtained green suspension of nickel (II) hydroxide at room temperature for 17 hours. The mixture is then filtered through a pressure filter under 1.4 atmospheres of nitrogen, washed three times with 500 ml of water each time and dried while gassing with nitrogen to produce nickel peroxide having a weight of 28 g. Iodometric titration: 6.9% of active oxygen.
Sample oxidation with 5.5 g of nickel peroxide: quantitative conversion.

EXAMPLE 12

Oxidation of geraniol [3,7-dimethyl-2,6-octadien-1-ol] to citral [3,7-dimethyl-2,6-octadienal]

15.4 g (0.1 mole) of geraniol in 250 ml of n-hexane are treated portionwise at −25° C to −30° C within 50 minutes while stirring with a total of 46 g of nickel peroxide (prepared by Example 3 and containing 7.3% of iodometrically detected active oxygen). The mixture is allowed to oxidise for a further 30 minutes at −25°to −30° C and then filtered under suction. After rinsingthe expended nickel peroxide with hexane at −25° C, the solvent is completely evaporated. The product is obtained as a colourless oil (13.9 g) which, according to gas and thinlayer chromatographic analysis, represents pure citral. It absorbs at 237 nm (ethanol) in the UV spectrum with a $E_1^1 = 1012$.

EXAMPLE 13

By the procedure of Example 12, 15.4 g of geraniol are oxidised at a temperature of −50° to −55° C. After 5 hours, the oxidation was stopped and there are obtained 13.4 g of pure citral.

EXAMPLE 14

By the procedure of Example 13, 15.4 g of geraniol was oxidized with 46 g of nickel peroxide in 250 ml of methylene chloride as the solvent, there was obtained a complete conversion of the geraniol to citral at −25° to −30° C within 9 minutes. The yield amounts to 14.9 g with a $E_1^1 = 1024$ (ethanol) at 237 nm.

EXAMPLE 15

Oxidation of benzyl alcohol to benzaldehyde 10.8 g (0.1 mole) of benzyl alcohol in 500 ml of methylene chloride are stirred at −20° C with a total of 61 g of nickel peroxide (prepared in Example 1 and containing 6.1% of active oxygen) in 6 portions. After an oxidation time of 4 hours, the nickel peroxide is filtered off and the solvent evaporated. There was obtained 9.8 g of product which, according to gas and thin-layer chromatographic analysis, represents pure benzaldehyde.

EXAMPLE 16

Oxidation of ethyl 8-hydroxy-2,6-dimethyl-octa-2,4,6-trien-1-oate 21 g of ethyl 8-hydroxy-2,6-dimethyl-octa-2,4,6-trien-1-oate in 500 ml of methylene chloride are stirred at −25° C for 2 hours with 50 g of nickel peroxide (prepared in Example 1 and containing 6.1% of active oxygen). The mixture is then filtered, the solution evaporated to 100 ml, treated with 250 ml of n-hexane and again evaporated to 100 ml. The residual solution is cooled to 50° C, seeded with crystals of ethyl 2,6-dimethyl-8-oxo-octa-2,4,6-trien-1 -oate and left to crystallise for 30 minutes at 0° C. After filtration under suction and drying of the crystals, there are obtained 16.5 g (79.5%) of pure ethyl 2,6-dimethyl-8-oxo-octa-2,4,6-trien-1-oate.

EXAMPLE 17

Oxidation of 8-hydroxy-2,6-dimethyl-octa-2,4,6-trien-1-al dimethylacetal.

42.4 g (0.2 mole) of 8-hydroxy-2,6-dimethyl-octa-2,4,6-trien-1-al dimethylacetal in 500 ml of methylene chloride are stirred at −20° to −25° C for 2 hours with 160 g of nickel peroxide (prepared in Example 1 and containing 6.1% of active oxygen). The mixture is then filtered off under suction, washed with 500 ml of methylene chloride at −20° C and the filtrate completely evaporated. There remain 40.9 g of crude 8,8-dimethoxy-3,7-dimethyl-octa-2,4,6-trien-1-al which are purified by distillation in a high vacuum at 0.04–0.05 mmHg. After separation of 2 g of pre-runnings (102°–106° C) there are obtained 33.4 g of purified aldehyde (104°–108° C), which are mixed first with 33 ml of n-hexane at 0° C and then crystallised for 6 hours at −20° C. The crystals are filtered off under suction, washed with n-hexane at −20° C and dried in vacuo at 30°–40° C, the pure aldehyde i.e. 8,8-dimethoxy-3,7-dimethyl-octa2,4,6-trien-1-al being obtained as a yellow crystalline powder (29.5g; 70.3%).

EXAMPLE 18

Oxidation of phytol 59.2 g (0.2 mole) of phytol in 500 ml of toluene are stirred at −25° to −30° C in 10 minute intervals with five times 18.6 g of nickel peroxide (prepared in Example 3 and containing 7.3% of active oxygen). The mixture is then stirred for a further 30 minutes at −25° to −30° C, filtered off under suction and washed with 500 ml of toluene at −30° C. The filtrate is evaporated on a rotary evaporator at 60° C, treated with 250 ml of ethanol and again completely evaporated to remove the toluene. There remain 57.3 g of phytal which, according to thin-layer chromatography, is pure and shows the expected extinction with $E_1^1 = 525$ in the UV (hexane) at 230 nm.

EXAMPLE 19

Oxidation of vitamin A alcohol 57.2 g (0.2 mole) of crystalline all-trans vitamin A alcohol are dissolved in 1 liter of methylene chloride. The solution is then stirred at −20° to −35° C in 10 minute intervals with a total of 90 g of nickel peroxide prepared in Example 4 in 5 portions. After the last portion has been introduced, the mixture is stirred for a further 15 minutes at −20° to −35° C, filtered off under suction and washed with a total of 1 liter of methylene chloride at −30° C. The residue collected on the filter has the spent nickel peroxide. The methylene chloride solution is subsequently concentrated to a volume of about 500 ml on a rotary evaporator. The residual solution is then treated with 500 ml of n-hexane, again evaporated to 500 ml, again treated with 500 ml of n-hexane and finally concentrated to a volume of 100 ml. The concentrate is cooled to 10° C, seeded with vitamin A aldehyde crystals and then left overnight at −20° C to completely crystallise out. The crystals are then filtered off under suction, washed with 250 ml of pentane at −20° C and dried in vacuo at 30° C in a constant weight. There are obtained 49 g (86%) of vitamin A aldehyde with the expected melting point of 63.5°–65° C and the UV value $E_1^1 = 1750$ at 366 nm (hexane).

EXAMPLE 20

Oxidation of β-ionol.

19.5 g (0.1 mole) of β-ionol [4-(2,6,6-trimethyl-1-cyclohexen-1-yl)-3-buten-2-ol] are boiled at reflux in 250 ml of pentane together with 42.5 g of nickel peroxide for 2.5 hours while stirring, a water separator being inserted between the reflux condenser and the reaction vessel. After 2.5 hours, starting material can no longer be detected in a thin-layer chromatogram and the β-ionone spot is seen as the main product, identical with an authentic comparative sample. The filtrate is then evaporated. There remain 19 g of an oily product which absorbs at 296 nm in the UV (ethanol) and according to the extinction ($E_1^1 - 500$) represents 92% β-ionone. [4-(2,6,6-trimethyl-1-cyclohexen-1-yl)-3-buten-2-one].

EXAMPLE 21

Regeneration of the expended nickel peroxide

Nickel peroxide residue collected in Example 19 was immediately stirred for 30 minutes at room temperature with 500 ml of methylene chloride, filtered off under suction, washed with 500 ml of methylene chloride and finally freed from the methylene chloride by washing with a total of 500 ml of water. The water-moist product is stirred with 400 ml of water, cooled to 0°–5° C and treated with a solution of 45 g of sodium hydroxide in 200 ml of water. Chlorine gas is then fed in at 0°–5° C within about 30 minutes until the pH measured with a glass electrode sinks from 13–14 to 9–11. The mixture is then stirred for a further 30 minutes at 0° C and a pH between 9–11. The thus-regenerated nickel peroxide is filtered through a pressure filter under nitrogen, washed with about 3 liters of water and finally dried in a nitrogen gas stream until a weight of ca 90 g has been reached. The thus-regenerated nickel peroxide is expediently stored in a refrigerator. It is analysed in the same manner and can be used for oxidations as a product freshly prepared from water-soluble nickel salts.

I claim:

1. A process for converting α, β-unsaturated alcohols to the corresponding α, β-unsaturated carbonyl compounds comprising treating said alcohol with a nickel peroxide oxidizing agent prepared by treating a nickel (III) hydroxide with a strong oxidizing agent in an aqueous medium to form nickel peroxide as a precipitate and drying said precipitate to a weight of at least 110 g. per mole of nickel (II) hydroxide in said starting material, with the oxidizing step of said nickel (II) hydroxide and the drying step of said precipitate being carried out in the absence of carbon dioxide and water soluble carbonates.

2. The process of claim 1 wherein said alcohol has the formula:

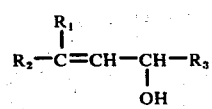

wherein $R_1$ is individually hydrogen or lower alkyl; $R_2$ is individually hydrocarbyl, cyclohydrocarbyl or cyclohydrocarbyl substituted hydrocarbyl; $R_1$ taken together with $R_2$ and their attached carbon atom form a cyclohydrocarbyl; $R_3$ is hydrogen, hydrocarbyl, cyclohydrocarbyl or cyclohydrocarbyl substituted hydrocarbyl; said hydrocarbyl and cyclohydrocarbyl being unsubstituted or substituted in one or more positions with lower alkyl, lower alkoxy, hydroxy, oxo, acetalized oxo, lower alkanoyl, aroyl, lower alkanoyloxy, or aroyloxy.

3. The process of claim 2 wherein said alcohol is geraniol.

4. The process of claim 2 wherein said alcohol is ethyl-8-hydroxy-2,6-dimethyl-octa-2,4,6-trien-1oate.

5. The process of claim 2 wherein said alcohol is Vitamin A alcohol.

6. The process of claim 2 wherein alcohol is 8-hydroxy-2,6-dimethyl-octa-2,4,6-trien-1-oate.

* * * * *